(12) United States Patent
Danenberg et al.

(10) Patent No.: US 6,428,963 B2
(45) Date of Patent: *Aug. 6, 2002

(54) ISOLATION OF RNA FROM FORMALIN-FIXED PARAFFIN-EMBEDDED TISSUE SPECIMENS

(75) Inventors: Kathleen Danenberg; Peter V. Danenberg, both of Altadena; Steven Swenson, Arcadia, all of CA (US)

(73) Assignee: University of Southern California, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/797,158

(22) Filed: Mar. 1, 2001

Related U.S. Application Data

(63) Continuation of application No. 09/469,338, filed on Dec. 20, 1999, now Pat. No. 6,248,535.

(51) Int. Cl.⁷ .......................... C12Q 1/68; A01N 1/00; G01N 1/30; G01N 33/48; C07H 21/00
(52) U.S. Cl. .......................... 435/6; 435/1.1; 435/40.5; 435/40.52; 435/91.1; 435/91.2; 536/25.4; 536/25.41
(58) Field of Search .......................... 435/6, 91.1, 1.1, 435/40.52, 3, 91.2; 536/23.1, 25.4, 25.41, 25.42; 530/419

(56) References Cited

U.S. PATENT DOCUMENTS

| | | | | |
|---|---|---|---|---|
| 5,707,802 A | * | 1/1998 | Sandhu et al. | 435/6 |
| 5,989,857 A | * | 11/1999 | Mundschenk | 435/91.1 |
| 6,248,535 B1 | * | 6/2001 | Danenberg et al. | 435/6 |

OTHER PUBLICATIONS

Miyauchi et al., Pathology International, Jun. 1998, vol. 48, pp. 428–432.*

* cited by examiner

*Primary Examiner*—W. Gary Jones
*Assistant Examiner*—Jehanne Souaya
(74) *Attorney, Agent, or Firm*—McCutchen, Doyle, Brown & Enersen, LLP

(57) ABSTRACT

Methods are disclosed for rapid, reliable and simple isolation of RNA from formalin-fixed paraffin-embedded tissue samples. RNA purified in this manner can be used to monitor gene expression levels. The tissue sample can be a tumor or other pathological tissue.

26 Claims, 8 Drawing Sheets

ISOLATION OF RNA FROM FORMALIN-FIXED PARAFFIN-EMBEDDED TISSUE SPECIMENS

CROSS-REFERENCE TO RELATED APPLICATION DATA

This application is a continuation of U.S. Ser. No. 09/469,338, filed Dec. 20, 1999 now U.S. Pat. No. 6,248,535.

GOVERNMENT SUPPORT

The government has certain rights in this invention pursuant to grant number R01 CA 71716 from the National Cancer Institute of the National Institutes of Health.

FIELD OF THE INVENTION

This invention relates to the field of purification of RNA, DNA and proteins from biological tissue samples.

BACKGROUND

The determination of gene expression levels in tissues is of great importance for accurately diagnosing human disease and is increasingly used to determine a patient's course of treatment. Pharmacogenomic methods can identify patients likely to respond to a particular drug and can lead the way to new therapeutic approaches.

For example, thymidylate synthase (TS) is an integral enzyme in DNA biosynthesis where it catalyzes the reductive methylation of deoxyuridine monophosphate (dUMP) to deoxythymidine monophosphate (dTMP) and provides the only route for de novo synthesis of pyrimidine nucleotides within the cell (Johnston et al., 1995). Thymidylate synthase is a target for chemotherapeutic drugs, most commonly the antifolate agent 5-fluorouracil (5-FU). As the most effective single agent for the treatment of colon, head and neck and breast cancers, the primary action of 5-FU is to inhibit TS activity, resulting in depletion of intracellular thymine levels and subsequently leading to cell death.

Considerable variation in TS expression has been reported among clinical tumor specimens from both primary tumors (Johnston et al., 1995; Lenz et al., 1995) and metastases (Farrugia et al., 1997; Leichmann et al., 1997). In colorectal cancer, for example, the ratio of TS expression in tumor tissue relative to normal gastrointestinal mucosal tissue has ranged from 2 to 10 (Ardalan and Zang, 1996).

Thymidylate synthase is also known to have clinical importance in the development of tumor resistance, as demonstrated by studies that have shown acute induction of TS protein and an increase in TS enzyme levels in neoplastic cells after exposure to 5-FU (Spears et al. 1982; Swain et al. 1989). The ability of a tumor to acutely overexpress TS in response to cytotoxic agents such as 5-FU may play a role in the development of fluorouracil resistance. Previous studies have shown that the levels of TS protein directly correlate with the effectiveness of 5-FU therapy, that there is a direct correlation between protein and RNA expression (Jackman et al., 1985) and that TS expression is a powerful prognostic marker in colorectal and breast cancer (Jackman et al., 1985; Horikoshi et al., 1992).

In advanced metastatic disease, both high TS mRNA, quantified by RT-PCR, and high TS protein expression, have been shown to predict a poor response to fluoropyrimidine-based therapy for colorectal (Johnston et al., 1995, Farrugia et al., 1997, Leichman et al., 1997), gastric (Lenz et al., 1995, Alexander et al., 1995), and head and neck (Johnston et al., 1997) cancers. A considerable overlap between responders and non-responders was often present in the low TS category, but patients with TS levels above the median were predominantly nonresponders. The predictive value of TS overexpression may be further enhanced if combined with other molecular characteristics such as levels of dihydropyrimidine dehydrogenase (DPD) and thymidine phosphorylase (TP) expression, replication error positive (RER+) status (Kitchens and Berger 1997), and p53 status (Lenz et al., 1997). Studies to date that have evaluated the expression of TS in human tumors suggest that the ability to predict response and outcome based upon TS expression in human tumors may provide the opportunity in the future to select patients most likely to benefit from TS-directed therapy.

Until now, quantitative tissue gene expression studies including those of TS expression have been limited to reverse transcriptase polymerase chain reaction (RT-PCR) amplification of RNA from frozen tissue. However, most pathological samples are not prepared as frozen tissues, but are routinely formalin-fixed and paraffin-embedded (FFPE) to allow for histological analysis and for archival storage. Gene expression levels can be monitored semi-quantitatively and indirectly in such fixed and embedded samples by using immunohistochemical staining to monitor protein expression levels. Because paraffin-embedded samples are widely available, rapid and reliable methods are needed for the isolation of nucleic acids, particularly RNA, from such samples.

A number of techniques exist for the purification of RNA from biological samples, but none are reliable for isolation of RNA from FFPE samples. For example, Chomczynski (U.S. Pat. No. 5,346,994) describes a method for purifyng RNA from tissues based on a liquid phase separation using phenol and guanidine isothiocyanate. A biological sample is homogenized in an aqueous solution of phenol and guanidine isothiocyanate and the homogenate thereafter mixed with chloroform. Following centrifugation, the homogenate separates into an organic phase, an interphase and an aqueous phase. Proteins are sequestered in the organic phase, DNA in the interphase, and RNA in the aqueous phase. RNA can be precipitated from the aqueous phase. This method does not provide for the reliable isolation of RNA from formalin-fixed paraffin-embedded tissue samples.

Other known techniques for isolating RNA typically utilize either guanidine salts or phenol extraction, as described for example in Sambrook, J. et al., (1989) at pp. 7.3–7.24, and in Ausubel, F. M. et al., (1994) at pp. 4.0.3–4.4.7. However, none of the known methods provide reproducible quantitative results in the isolation of RNA from paraffin-embedded tissue samples.

Techniques for the isolation of RNA from paraffin-embedded tissues are particularly needed for the study of gene expression in tumor tissues. Expression levels of certain receptors or enzymes can indicate the likelihood of success of a particular treatment.

Truly quantitative TS gene expression studies have been limited to RT-PCR from frozen tissue, whereas semi-quantitative monitoring of TS protein expression in archival pathological material fixed onto glass slides has been available via immunohistochemical staining. Because of limitations in isolating RNA from archival pathological material, quantitative techniques for measuring gene expression levels from such samples were heretofore unavailable.

SUMMARY

One aspect of the present invention is to provide a reliable method for the isolation of RNA, DNA or proteins from samples of biological tissues. The invention also provides simple, efficient and reproducible methods for the isolation of RNA, DNA or proteins from tissue that has been embedded in paraffin.

The invention provides methods of purifying RNA from a biological tissue sample by heating the sample for about 5 to about 120 minutes at a temperature of between about 50 and about 100° C. in a solution of an effective concentration of a chaotropic agent. In one embodiment, the chaotropic agent is a guanidinium compound. RNA is then recovered from said solution. For example, RNA recovery can be accomplished by chloroform extraction.

In a method of the invention, RNA is isolated from an archival pathological sample. In one embodiment, a paraffin-embedded sample is first deparaffinized. An exemplary deparaffinization method involves washing the paraffinized sample with an organic solvent, preferably xylene. Deparaffinized samples can be rehydrated with an aqueous solution of a lower alcohol. Suitable lower alcohols include, methanol, ethanol, propanols, and butanols. In one embodiment, deparaffinized samples are rehydrated with successive washes with lower alcoholic solutions of decreasing concentration. In another embodiment, the sample is simultaneously deparaffinized and rehydrated.

The deparaffinized samples can be homogenized using mechanical, sonic or other means of homogenization. In one embodiment, the rehydrated samples are homogenized in a solution comprising a chaotropic agent, such as guanidinium thiocyanate (also sold as guanidinium isothiocyanate).

The homogenized samples are heated to a temperature in the range of about 50 to about 100° C. in a chaotropic solution, comprising an effective amount of a chaotropic agent. In one embodiment, the chaotropic agent is a guanidinium compound. A preferred chaotropic agent is guanidinium thiocyanate.

RNA is then recovered from the solution by, for example, phenol chloroform extraction, ion exchange chromatography or size-exclusion chromatography.

RNA may then be further purified using the techniques of extraction, electrophoresis, chromatography, precipitation or other suitable techniques.

RNA isolated by the methods of the invention is suitable for a number of applications in molecular biology including reverse transcription with random primers to provide cDNA libraries.

Purified RNA can be used to determine the level of gene expression in a formalin-fixed paraffin-embedded tissue sample by reverse transcription, polymerase chain reaction (RT-PCR) amplification. Using appropriate PCR primers the expression level of any messenger RNA can be determined by the methods of the invention. The quantitative RT-PCR technique allows for the comparison of protein expression levels in paraffin-embedded (via immunohistochemistry) with gene expression levels (using RT-PCR) in the same sample.

The methods of the invention are applicable to a wide range of tissue and tumor types and target genes and so can be used for assessment of treatment and as a diagnostic tool in a range of cancers including breast, head and neck, esophageal, colorectal, and others. A particularly preferred gene for the methods of the invention is the thymidylate synthase gene. The methods of the invention achieved reproducible quantification of TS gene expression in FFPE tissues, comparable to those derived from frozen tissue.

DETAILED DESCRIPTION

Figure 1:
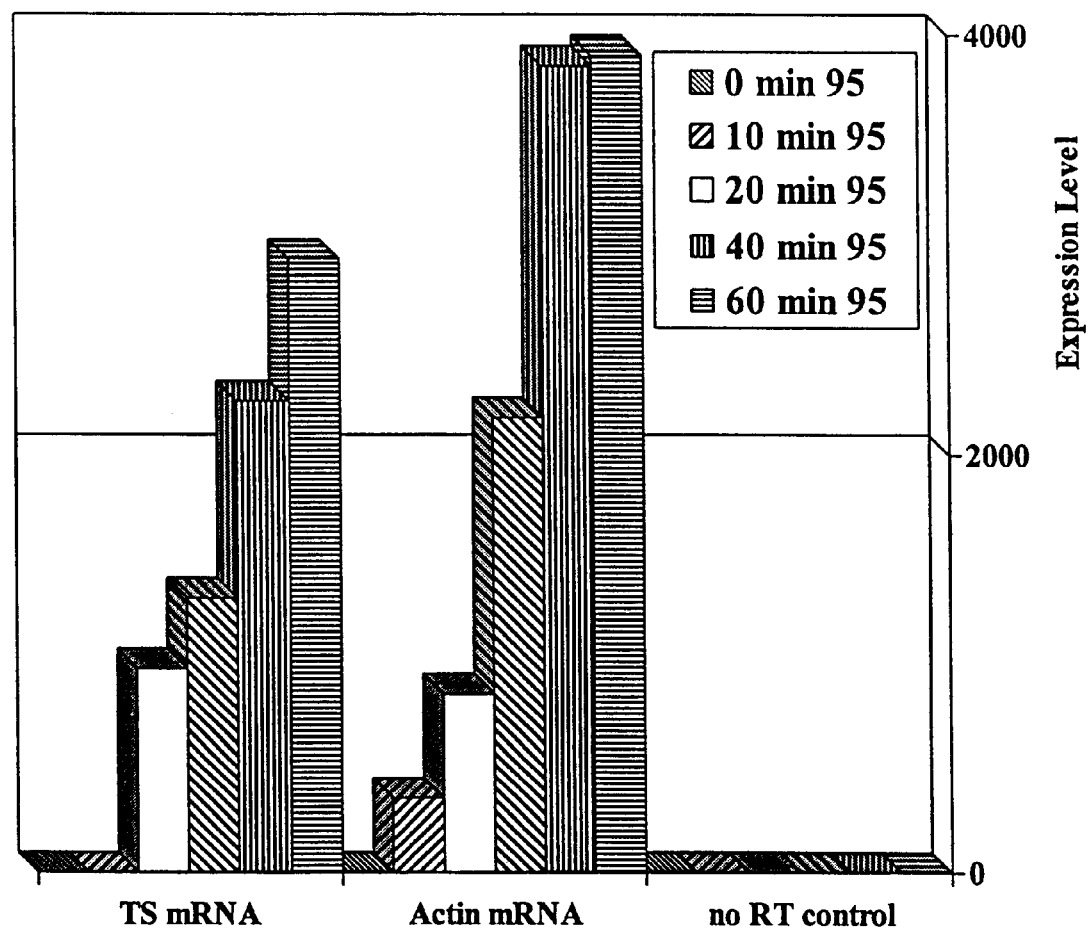
FIG. 1 shows level of $\beta$-Actin and TS expression at various heating times. These data show that without the heating step, there is a minimal yield of RNA extracted from the paraffin.

The methods of the instant invention involve purification of RNA from biological samples. In one embodiment, samples are paraffin-embedded tissue samples and the method involves deparaffinization of embedded samples, homogenization of the deparaffinized tissue and heating of the homogenized tissue at a temperature in the range of about 50 to about 100° C. for a time period of between about 5 minutes to about 120 minutes in a chaotropic solution containing an effective amount of a guanidinium compound. This heating step increases the amount of cDNA that are amplified from the specimen by up to 1000-fold over samples that are not heated.

While frozen tumor tissue is not widely available, paraffin blocks are routinely prepared from every type of tumor after surgery, allowing large-scale retrospective investigations of TS expression and chemotherapy response to be performed.

Moreover, the technique can be applied to any of a wide range of tumor types and to an unlimited range of target genes. This has implications for the future preparation of individual tumor "gene expression profiles" whereby expression levels could be determined in individual patient samples for a range of genes that are known to influence clinical outcome and response to various chemotherapeutic agents. Automated real-time PCR from FFPE sample allows for the targeting of treatment to individual tumors.

Tissue Samples

RNA can be isolated from any biological sample using the methods of the invention. Biological samples are often fixed with a fixative. Aldehyde fixatives such as formalin (formaldehyde) and glutaraldehyde are typically used. Tissue samples fixed using other fixation techniques such as alcohol immersion (Battifora and Kopinski, J. Histochem. Cytochem. (1986) 34:1095) are also suitable. The samples used are also embedded in paraffin. RNA can be isolated any paraffin-embedded biological tissue sample by the methods of the invention. In one embodiment, the samples are both formalin-fixed and paraffin-embedded.

Deparaffinization of Samples

Deparaffinization removes the bulk of paraffin from the paraffin-embedded sample. A number of techniques for deparaffinization are known and any suitable technique can be used with the present invention. The preferred method of the invention utilizes washing with an organic solvent to dissolve the paraffin. Such solvents are able to remove paraffin effectively from the tissue sample without adversely affecting RNA isolation. Suitable solvents can be chosen from solvents such as benzene, toluene, ethylbenzene, xylenes, and mixtures thereof. A xylene is the preferred solvent for use in the methods of the invention. Solvents alone or in combination in the methods of the invention are preferably of high purity, usually greater than 99%.

Paraffin is typically removed by washing with an organic solvent, with vigorous mixing followed by centrifugation. Samples are centrifuged at a speed sufficient to cause the tissue to pellet in the tube, usually at about 10,000 to about 20,000×g. After centrifugation, the organic solvent supernatant is discarded. One of skill in the art of histology will recognize that the volume of organic solvent used and the number of washes necessary will depend on the size of the sample and the amount of paraffin to be removed. The more paraffin to be removed, the more washes that will be necessary. Typically, a sample will be washed between 1 and about 10 times, and preferably, between about two and about four times. A typical volume of organic solvent is about 500 $\mu$L for a 10 $\mu$m tissue specimen.

Other methods for deparaffinization known to one of skill in the art may also be used in the method of the invention. Such methods include direct melting (Baneijee et al., 1995).

Samples are preferably rehydrated after deparaffinization. The preferred method for rehydration is step-wise washing with aqueous lower alcoholic solutions of decreasing concentration. Ethanol is a preferred lower alcohol for rehydration. Other alcohols may also be suitable for use with the invention including methanol, isopropanol and other similar alcohols in the C1–C5 range. The sample is alternatively vigorously mixed with alcoholic solutions and centrifuged. In a preferred embodiment, the concentration range of alcohol is decreased stepwise from about 100% to about 70% in water over about three to five incremental steps, where the change in solution concentration at each step is usually less than about 10% (i.e., the sequence: 100%, 95%, 90%, 80%, 70%). In another embodiment, deparaffinization and rehydration are carried out simultaneously using a reagent such as EZ-DEWAX (BioGenex, San Ramon, Calif.).

Homogenization

Deparaffinized, rehydrated samples can be homogenized by any standard mechanical, sonic or other suitable technique. Tissue homogenization is preferably carried out with a mechanical tissue homogenizers according to standard procedures. A number of commercially available homogenizers are suitable for use with the invention including: Ultra-Turrax homogenizer (IKA-Works, Inc., Wilmington, N.C.); Tissumizer (Tekmar-Dohrmann, Cincinnati, Ohio); and Polytron (Brinkmann, Westbury, N.Y.).

In one embodiment, the sample is homogenized in the presence of a chaotropic agent. Chaotropic agents are chosen such that at an effective concentration RNA is purified from a paraffin-embedded sample in an amount of greater than about 10 fold that isolated in the absence of a chaotropic agent. Chaotropic agents include: guanidinium compounds, urea, formarnide, potassium iodode, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and $\beta$-mercaptoethanol (BME). The chaotropic solution may also contain RNAse inhibitors.

Heating

Samples are heated in the chaotropic solution at a temperature of about 60° C. to about 100° C. for about 5 minutes to about 2 hours. Alternatively, samples are heated in the chaotropic solution at a temperature of about 50° C. to about 100° C. for about 5 minutes to about 2 hours. Heating times are typically chosen such that the amount of RNA purified is at least about 100-fold higher than for unheated samples, and more preferably about 1000-fold higher. In a preferred embodiment, the sample is heated for about 20 minutes at a temperature of from about 75 to about 100° C. More preferably, the sample is heated for 30 to 60 minutes at about 95° C.

RNA Recovery

RNA can be recovered from the chaotropic solution after heating by any suitable technique that results in isolation of the RNA from at least one component of the chaotropic solution. RNA can be recovered from the chaotropic solution by extraction with an organic solvent, chloroform extraction, phenol-chloroform extraction, precipitation with ethanol, isopropanol or any other lower alcohol, by chromatography including ion exchange chromatography, size exclusion chromatography, silica gel chromatography and reversed phase chromatography, or by electrophoretic methods, including polyacrylamide gel electrophoresis and agarose gel electrophoresis, as will be apparent to one of skill in the art. RNA is preferably recovered from the chaotropic solution using phenol chloroform extraction.

Following RNA recovery, the RNA may optionally by further purified. Further purification results in RNA that is substantially free from contaminating DNA or proteins. Further purification may be accomplished by any of the aforementioned techniques for RNA recovery. RNA is preferably purified by precipitation using a lower alcohol, especially with ethanol or with isopropanol. Precipitation is preferably carried out in the presence of a carrier such as glycogen that facilitates precipitation.

DNA and Protein Recovery

The methods of the invention can also be used to purify DNA or protein from the tissue sample. After mixing a sample with an organic solvent, such as chloroform, and following centrifugation, the solution has three phases, a lower organic phase, an interphase, and an upper aqueous phase. With an appropriate chaotropic agent, particularly with a guanidinium compound, the biological components of the sample will segregate into the three phases. The upper aqueous phase will contain RNA, while the interphase will contain DNA and the organic phase will contain proteins. One of skill in the art will recognize that the methods of the invention are suitable for recovering both the DNA and protein phases as well as that containing the RNA. DNA recovery is enhanced by the methods of the invention.

Purified RNA

RNA purified by the methods of the invention is suitable for a variety of purposes and molecular biology procedures including, but not limited to: reverse transcription to cDNA; producing radioactively, fluorescently or otherwise labeled cDNA for analysis on gene chips, oligonucleotide microarrays and the like; electrophoresis by acrylamide or agarose gel electrophoresis; purification by chromatography (e.g. ion exchange, silica gel, reversed phase, or size exclusion chromatography); hybridization with nucleic acid probes; and fragmentation by mechanical, sonic or other means.

EXAMPLES

Materials and Methods

These materials and methods are common to the following examples.

Sample Preparation. The characteristics of the human cell lines SK1, H157, A431, HT29, HCC298 and HH30 have been described previously. Cells were removed from their monolayer by trypsinization and pelleted by centrifugation at 3000 rpm for 5 minutes. Cell pellets were either frozen at −70° C. or fixed in formalin for 24h, then embedded in paraffin.

Representative sections of tumor tissue were obtained at the time of surgery, fixed in formalin and embedded in paraffin by procedures common to most clinical pathology laboratories. Cross-sections of tissue (5 $\mu$m) were cut using a microtome.

RNA Isolation. RNA was isolated from paraffin embedded tissue as follows. A single 5 $\mu$m section of paraffmized tissue was placed in an Eppendorf tube and deparaffinized by two 15 minute washes with xylene. The tissue was rehydrated by successive 15 minute washes with graded alcohols (100%, 95%, 80% and 70%). The resulting pellet was suspended in 4M guanidine isothiocyanate with 0.5% sarcosine and 20 mM dithiothreitol (DTT). The suspension was homogenized and then heated to from about 50 to about 95° C. for 0 to 60 minutes; a zero heating time-point, was included as a control for each sample. Sodium acetate (pH 4.0) was added to 0.2 M and the solution was extracted with phenol/chloroform and precipitated with isopropanol and 10 mg glycogen. After centrifugation (13000 rpm, 4° C., 15 min) the RNA pellet was washed twice with 1 mL of 75% ethanol then resuspended in RNase-free water.

Reverse transcription (RT). After heating, total RNA was converted to cDNA using random hexamers. RT conditions were as have been previously described for frozen tissue (Horikoshi et al., 1992). Controls omitting the reverse transcriptase (No-RT) were prepared for each sample.

Real-Time PCR quantification of TS and $\beta$-actin gene expression using the Perkin Elmer Cetus 7700 PCR Machine (Taqman). The quantitation of mRNA levels was carried out using real-time PCR based on a fluorescence detection method as described previously (Heid et al., 1996; Eads et al., 1999). cDNA was prepared as described above. The cDNA of interest and the reference cDNA were amplified separately using a probe with a 5'-fluorescent reporter dye (6FAM) and a 3'-quencher dye (TAMRA). The 5'-exonuclease activity of TAQ polymerase cleaves the probe and releases the reporter molecule, the fluorescence of which is detected by the ABI Prism Sequence Detection System (Taqman). After crossing a fluorescence detection threshold, the PCR amplification results in a fluorescent signal proportional to the amount of PCR product generated. Initial template concentration was determined from the cycle number at which the fluorescent signal crossed a threshold in the exponential phase of the PCR reaction. Relative gene expression was determined based on the threshold cycles of the gene of interest and the reference gene. Use of a reference gene avoids the need to quantitate the RNA directly, which could be a major source of error.

The primer and probe sequences were as follows: TS: SEQ ID NO: 1: GGC CTC GGT GTG CCT TT; SEQ ID NO: 2: AAC ATC GCC AGC TAC GCC CTG C; SEQ ED NO: 3: GAT GTG CGC AAT CAT GTA CGT. $\beta$-actin: SEQ ID NO: 4: TGA GCG CGG CTA CAG CTT; SEQ ID NO: 5: ACC ACC ACG GCC GAG CGG; SEQ ID NO: 6: TCC TTA ATG TCA CGC ACG ATT T. For the real-time PCR experiments, as discussed above, the reporter oligonucleotide (SEQ ID NOS: 2 and 5) were 5' labelled with 6FAM and were 3' labelled with TAMRA.

For each PCR, a "No Reverse Transcriptase" (NRT or No-RT) control was included. The purpose of this reaction was to correct for any background amplification, derived from residual genomic DNA contamination. Hence, each overall value for TS and $\beta$-actin is calculated as the RT value minus the NRT value (RT-NRT).

Statistical Analysis. Non-parametric comparison of means test were performed to determine if differences in TS levels between frozen tissue and FFPE samples of the same tumor were significant or non-significant.

EXAMPLE 1

General RNA Isolation Procedure

RNA was extracted from paraffin-embedded tissue by the following general procedure.

A. Deparaffinization and hydration of sections:

(1) A portion of an approximately 10 $\mu$M section is placed in a 1.5 mL plastic centrifuge tube.

(2) 600 $\mu$L of xylene are added and the mixture is shaken vigorously for about 10 minutes at room temperature (roughly 20 to 25° C.).

(3) The sample is centrifuged for about 7 minutes at room temperature at the maximum speed of the bench top centrifuge (about 10–20,000×g).

(4) Steps 2 and 3 are repeated until the majority of paraffin has been dissolved. Two or more times are normally required depending on the amount of paraffin included in the original sample portion.

(5) The xylene solution is removed by vigorously shaking with a lower alcohol, preferably with 100% ethanol (about 600 µL) for about 3 minutes.

(6) The tube is centrifuged for about 7 minutes as in step (3). The supernatant is decanted and discarded. The pellet becomes white.

(7) Steps 5 and 6 are repeated with successively more dilute ethanol solutions: first with about 95% ethanol, then with about 80% and finally with about 70% ethanol.

(8) The sample is centrifuged for 7 minutes at room temperature as in step (3). The supernatant is discarded and the pellet is allowed to dry at room temperature for about 5 minutes.

B. RNA Isolation with Phenol-Chloroform (1) 400 µL guanidine isothiocyanate solution including 0.5% sarcosine and 8 µL 1 M dithiothreitol is added.

(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).

(3) The sample is then heated at about 95° C. for about 5–20 minutes. It is preferable to pierce the cap of the tube containing the sample before heating with a fine gauge needle. Alternatively, the cap may be affixed with a plastic clamp or with laboratory film.

(4) The sample is then extracted with 50 µL 2 M sodium acetate at pH 4.0 and 600 µL of phenol/chloroform/isoamyl alcohol (10:1.93:0.036), prepared fresh by mixing 18 mL phenol with 3.6 mL of a 1:49 isoamyl alcohol:chloroforn solution. The solution is shaken vigorously for about 10 seconds then cooled on ice for about 15 minutes.

(5) The solution is centrifuged for about 7 minutes at maximum speed. The upper (aqueous) phase is transferred to a new tube.

(6) The RNA is precipitated with about 10 µL glycogen and with 400 µL isopropanol for 30 minutes at −20° C.

(7) The RNA is pelleted by centrifugation for about 7 minutes in a benchtop centrifuge at maximum speed; the supernatant is decanted and discarded; and the pellet washed with approximately 500 µL of about 70 to 75% ethanol.

(8) The sample is centrifuged again for 7 minutes at maximum speed. The supernatant is decanted and the pellet air dried. The pellet is then dissolved in an appropriate buffer for further experiments (e.g. 50 µL 5 mM Tris chloride, pH 8.0).

EXAMPLE 2

Heating Time

This example illustrates the effect of time of heating on the yield of RNA.

As illustrated in FIG. 1, heating of the chaotropic solution at 95° C. prior to precipitation and reverse transcription significantly increased the efficiency of detection of TS and β-actin targets. When no heating step was included, neither TS nor β-actin could be detected (0 min. time points). After 20 minutes at 95° C. both transcripts were detectable; a further increase of heating time to 60 minutes resulted in a 3-fold increase in sensitivity of detection for TS and 4.5-fold increase for β-actin. (NRT=No Reverse Transcriptase control, RT-NRT=overall relative gene expression level, i.e. Reverse Transcriptase minus No Reverse Transcriptase).

Figure 2:
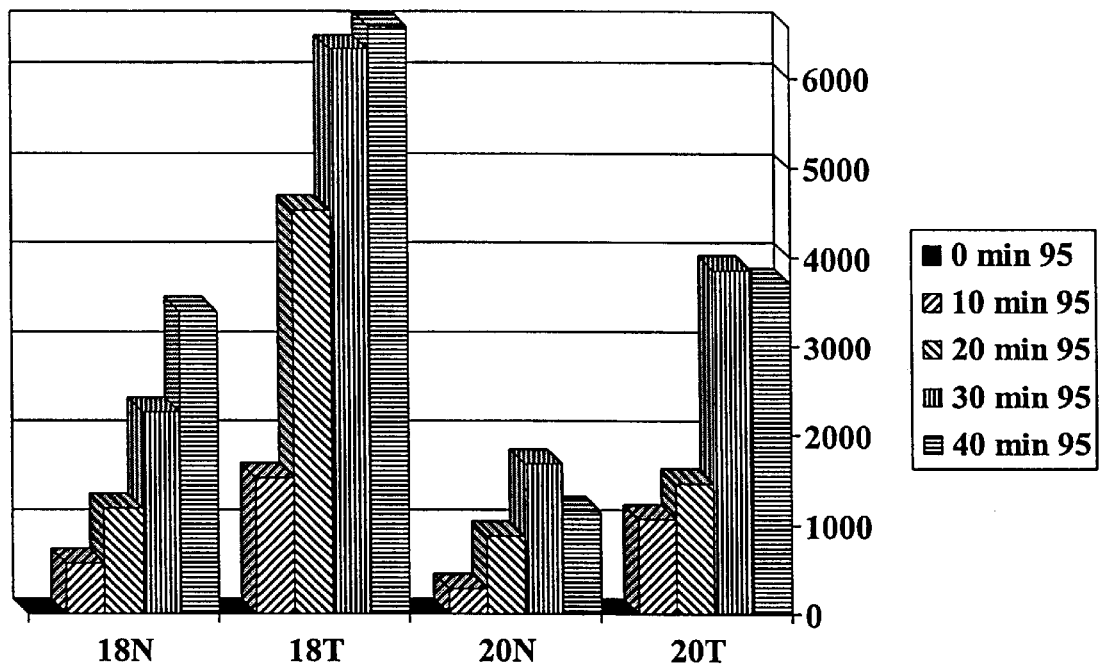
FIG. 2 shows the level of $\beta$-actin expression in normal (N) or tumorous (T) tissue from colorectal cancer patients as determined by quantitative PCR from RNA extracted at 95° C. for zero to 40 minutes. These data suggest 30 min as an optimal heating time.

FIG. 2 illustrates the amount of RNA expression of the β-actin gene in normal (N) and tumorous (T) tissue. The samples were heated at 95° C. for periods ranging from zero to 40 minutes. A preferred heating time of about 30 minutes is observed for most samples.

Figure 3:
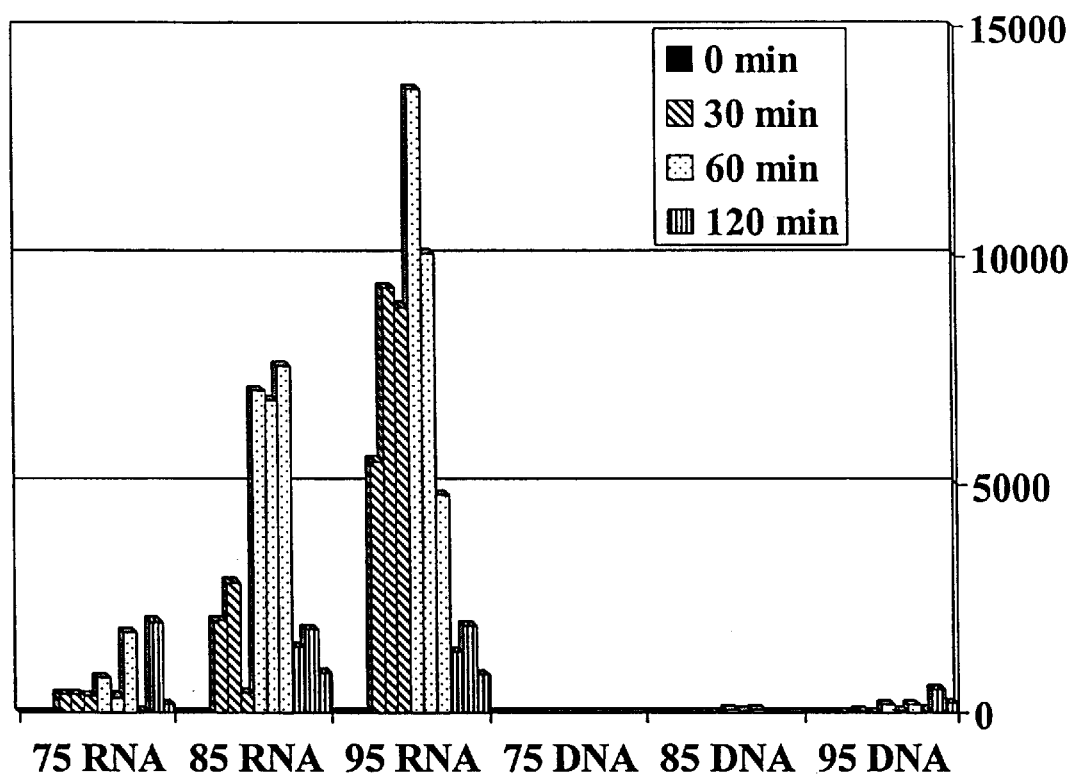
FIG. 3 shows the effect of both temperature and time on the yield of $\beta$-actin RNA and on the isolation of DNA. These data show that at longer heating times (between 60 and 120 min), RNA undergoes degradation while there is an increase in contaminating DNA capable of generating a DNA PCR signal. The bars represent values of triplicate experiments done at the various times and temperatures indicated.

FIG. 3 shows that at heating times longer than about 60 min, the amount of RNA extracted starts to decrease, suggesting thermal degradation of the RNA, whereas the amount of DNA extracted starts to increase. This is undesirable because the presence of DNA can give a spurious PCR signal in some cases.

EXAMPLE 3

Heating Solutions

This example illustrates that heating the RNA solution in the presence of a chaotropic agent is important for obtaining high yields of RNA. This was an RT-PCR experiment using detection of β-actin gene expression as a measure of relative amounts of RNA isolated in various solutions.

Figure 4:
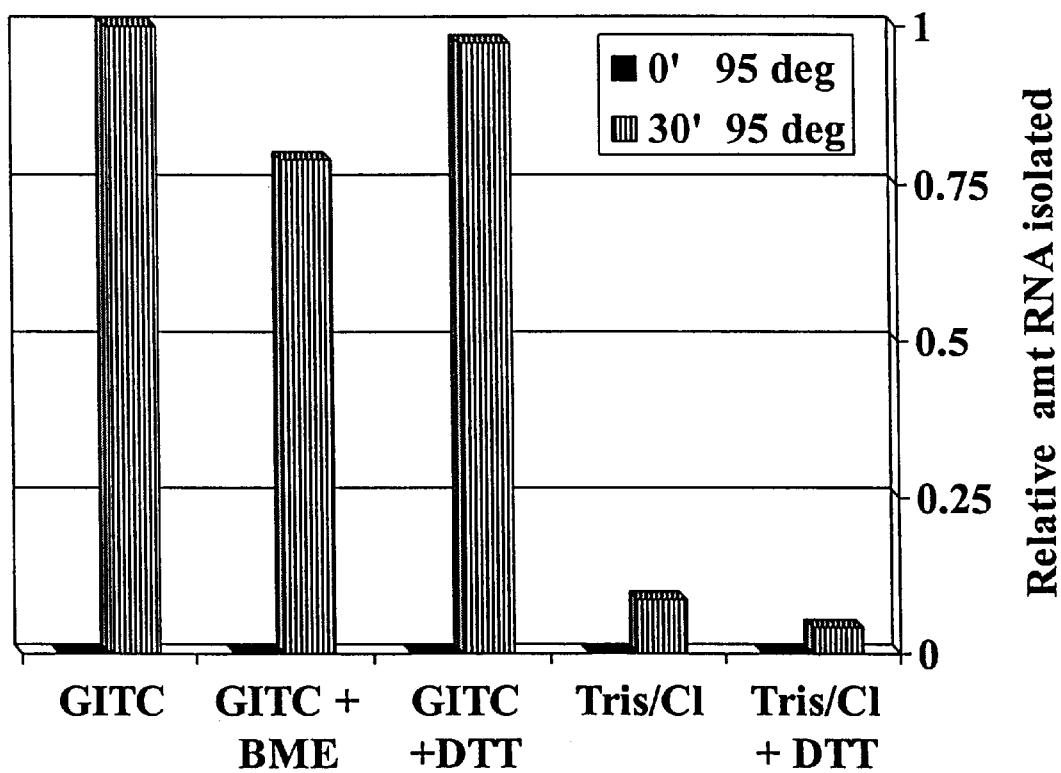
FIG. 4 shows the effect of various heating solutions on the yield of isolated RNA. These data show that the chaotrope in the solution, in this case guanidinium isothiocyanate (GITC), is the essential component of the RNA extraction solution, without which the yield of extracted RNA is at least 10-fold lower.

Clinical specimens of esophageal cancer FFPE tissue samples were treated according to the methods described above, with the exception that the initial pellet obtained after deparaffinization was dissolved or suspended in either 4M guanidinium isothiocyanate (GITC), 4M guanidinium isothiocyanate+100 µM β-mercaptoethanol (GITC+BME), 4M guanidinium isothiocyanate+20 µM dithiothreitol (GITC+DTT) or in Tris-Cl buffer (10 mM pH 7.5) or Tris-Cl buffer+20 pM DTT (Tris/Cl+DTT). The samples were then heated to 95° C. for 30 minutes or not heated (0 min, 95° C.). The Tris/Cl samples were then treated with 4M guanidinium isothiocyanate. RNA levels were determined by RT-PCR and real time PCR detection of β-Actin. As shown in FIG. 4, the presence of the chaotropic agent guanidinium isothiocyanate when heating was important for high yield recovery of RNA. The presence of a reducing agent, such as DTT or BME, is not essential for high yield recovery of RNA. The 4M guanidinium isothiocyanate solution contains 50 mM Tris-HCl (pH 7.5), 25 mM EDTA and 0.5% Sarcosine.

EXAMPLE 4

Comparison of Gene Expression Values Determined in FFPE and Frozen Tissue from the Same Sources This example shows that the methods of the present invention provide values for gene expressions from formalin-fixed paraffin-embedded samples equivalent to those obtained from frozen tissue.

Figure 5:
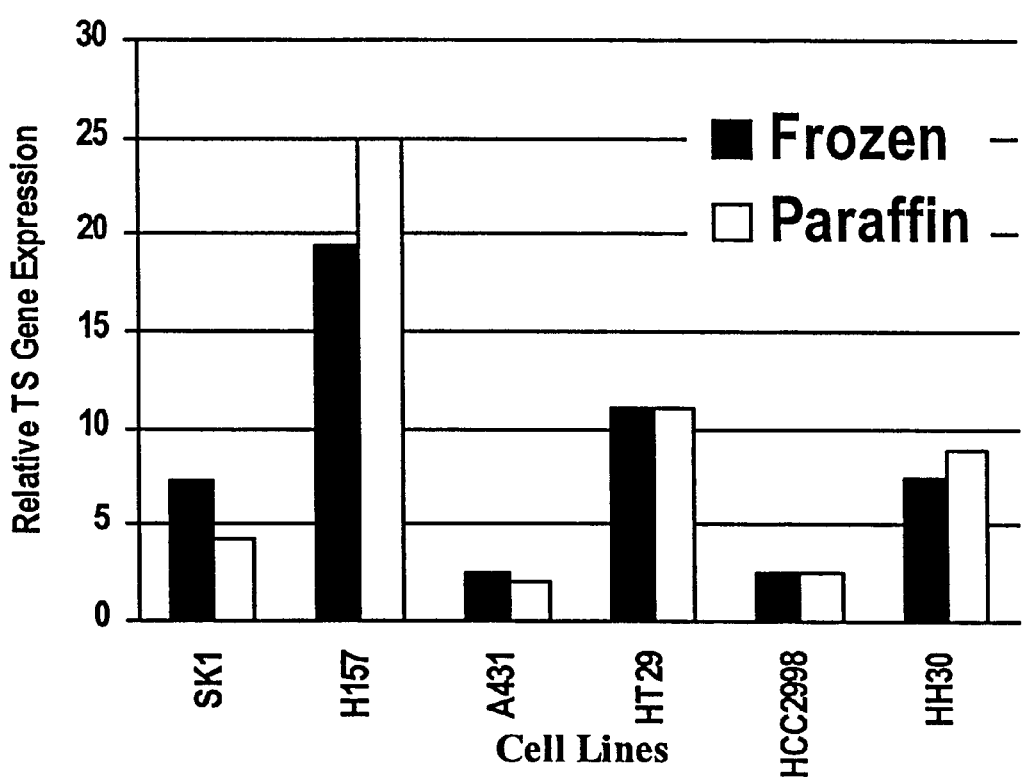
FIG. 5 shows a comparison of relative TS gene expression from paraffin-embedded (white bars) and frozen cell pellets (black bars) from six cell lines. These data show that analysis of paraffin-extracted RNA reliably reflects gene expression values in fresh-frozen tissue.

Samples from six cell lines were FFPE-treated and TS quantitation performed using the methods of the invention (including heating at 95° C. for 30 minutes). The resulting relative TS values (FIG. 5) were compared with those obtained from frozen cell pellets using known methods. Relative TS expression levels were 3.0–19.5 (mean=8.5) in frozen cells versus 3.0–25.0 (mean=9.0) in FFPE samples. Statistical analysis of the difference between the two means revealed a p value of 0.726, indicating that there is no significant difference in the TS values obtained from frozen cell pellets using the original RT-PCR methods and those obtained from FFPE cell pellets using the methods of the invention.

Figure 6:
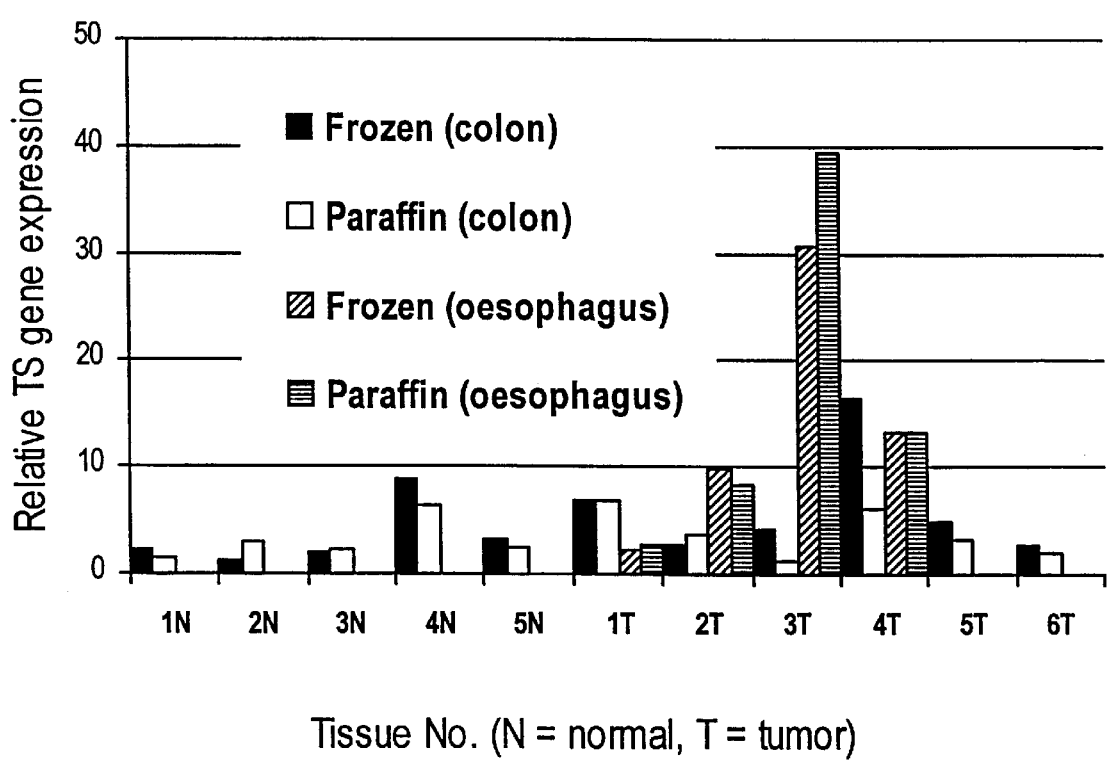
FIG. 6 shows a comparison of TS gene expression levels in normal or tumorous colon and tumorous esophageal tissues that were either formalin-fixed and paraffin-embedded or frozen.

RNA expression levels in samples of tumorous tissues and of normal (non-tumorous) tissues also were equivalent regardless of whether the samples were formalin-fixed and paraffin-embedded or frozen. Five normal and 6 tumor colon tissues and 4 esophageal tumor tissues, were compared for relative TS gene expression in matching paraffin and frozen tissue (FT) as above. Results are illustrated in FIG. 6. No significant difference was found between the levels of TS found in frozen tissue samples and the TS values found in FFPE samples of the same tissue. This was true for both colon and esophageal tissue types (mean FT samples colon= 3.46, mean FFPE samples colon=3.06, p=0.395; mean FT samples esophagus=13.9, mean FFPE samples esophagus= 15.93, p=0.21).

EXAMPLE 5

Comparison of TS Levels in Responsive and Non-Responsive Tumor Tissues

Figure 7:
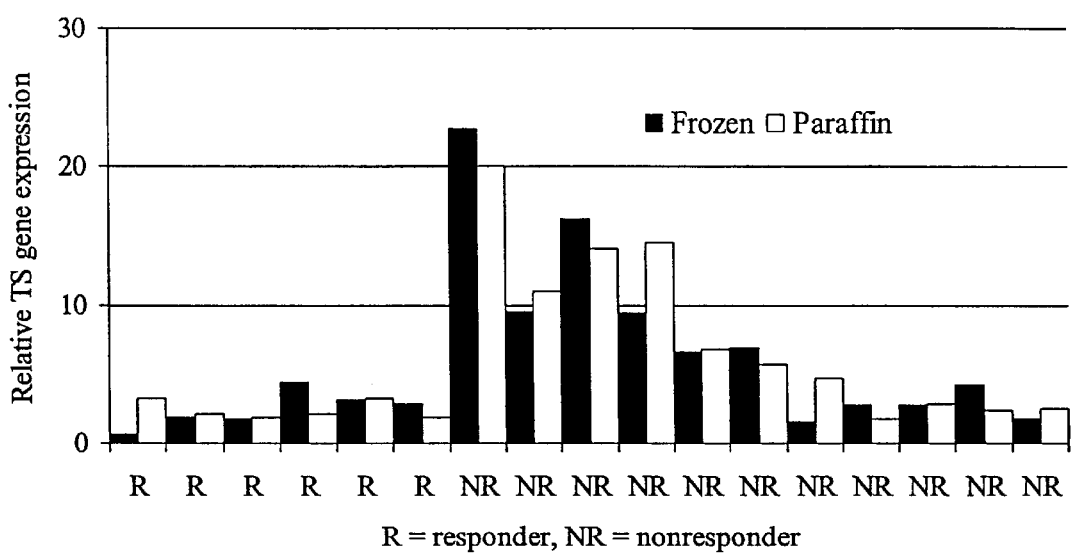
FIG. 7 shows TS/$\beta$-actin ratios determined in paraffin sections from patients whose response to 5-FU/LV was previously linked to TS gene expression.

Correlation of TS levels in frozen tissue and matching FFPE samples with response to 5-FU/Leucovorin (LV) in stage IV colon cancer. Previous reports based on RT-PCR data derived from frozen tissue found that high levels of TS in tumors (relative gene expression $\geq 4.0$) were indicative of a poor response to TS treatment. Responsive tumors could be characterized as expressing lower levels of TS. TS/β-actin ratios were determined in paraffin sections from 17 patients whose response to 5-FU/LV had previously been linked to TS gene expression via analysis of frozen tissue samples (FIG. 7). Of the 17, 6 were known to be responsive to TS and 11 were known to have been poor responders to TS treatment. It was found that the TS results with matching paraffin tissue would also have predicted response to this therapy (mean responders FT=2.87, mean responders FFPE=2.37, p=0.641: mean nonresponders FT=7.66, mean non-responders FFPE=7.84 p=0.537). There was no significant difference between the TS levels derived from frozen tissue and those derived from matching FFPE tissues.

EXAMPLE 6

TS Gene Expression Levels in Primary Colon Cancer and a Liver Metastasis

This example shows an analysis of TS, and other gene expression, in a primary colon tumor and in a recurrent liver metastasis from the same patient.

Figure 8:
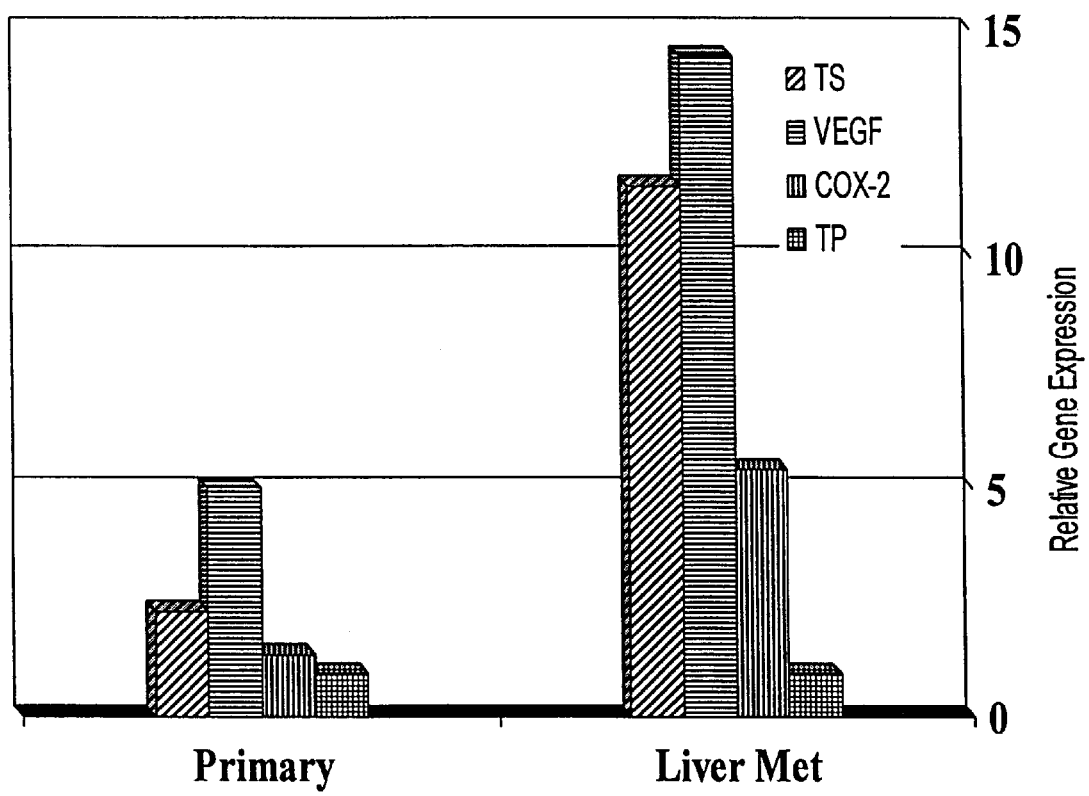
FIG. 8 shows the expression levels of four malignancy marker genes (TS; thymidine phosphorylase (TP); cyclooxygenase-2 (COX-2); and vascular endothelial growth factor (VEGF)) in FFPE samples of a primary colon cancer and a liver metastasis that recurred a year later in the same patient. These data show that, as might be expected, three of the four malignancy markers are elevated in the metastatic tumor tissue.

FIG. 8 shows the expression levels of four genes: TS; TP; cyclooxygenase-2 (COX-2); and vascular endothelial growth factor (VEGF) in FFPE samples of a primary colon cancer and a liver metastasis (met) from the same patient which recurred a year later. The findings suggest that, while the primary tumor was sensitive to 5-FU therapy (TS=2.32), the metastasis will be refractory (TS met 11.58). COX-2 and VEGF expression levels correlate with the published indications that they are increased in expression in aggressive disease, and coregulated. (Cox-2 primary=1.35; COX-2 met=5.4; VEGF primary=5.02; VEGF met=14.4.) RNA was isolated as described from a 5 µM FFPE section of the primary colon cancer and from an FFPE section of the liver metastasis. Relative TS gene expression in the responsive primary tumor was 2.32 compared to 11.58 in the metastatic disease (FIG. 8). This 5-fold increase in TS expression, as determined by the RT-PCR methods reported here, indicates that the secondary disease will not respond to 5-FU and suggests an alternative therapy such as CPT-11 may be appropriate.

All references cited herein are hereby incorporated by reference in their entirety.

REFERENCES

Ardalan, B. and Dang, Z. (1996) *Proc. Annu. Meet. Am. Assoc. Cancer Res.* 37:A1376.

Ausubel, F. M. et al., "Current Protocols In Molecular Biology", John Wiley & Sons, Inc., vol. 1, pp. 2.2.1–2.4.5 (1994).

Bannerjee, S. K., Makdisi, W. F., Weston, A. P., Mitchell, S. M., and Campbell, D. R. (1995) *Biotechniques*, 18:768–773.

Chomczynski et al., "Single-Step Method of RNA Isolation by Acid Guanidinium Thiocyanate-Phenol-Chloroform Extraction," *Analytical Biochemistry*, 162:156–159 (1987).

Eads, C. A., Danenberg, K. D., Kawakami, K., Saltz, L. B., Danenberg, P. V. and Laird, P. W. (1999) CpG island hypermethylation in humancolorectal tumors is not associated with DNA methyltransferse overexpression. *Cancer Res.*, 59: 2302–2306.

Farrugia, D. Cunningham D. Danenberg P. Danenberg K. Metzger R. Mitchell F. MacVicar D. McCarthy K. Aherne G W. Norman A. Jackman A L. (1997) *Proc. Annu. Meet Am. Assoc. Cancer Res.* 38:A4132.

Heid, C. A., Stevens, J., Livak, K. J. and Williams, P. M. (1996) Real-time quantitative PCR. *Genome Res.* 6:986–994.

Horikoshi, T., Danenberg, K. D., Stadlbauer, T. H. W., Volkenandt, M., Shea, L. L. C., Aigner, K., Gustavsson, B., Leichman, L., Frosing, R., Ray, M., Gibson, N. W., Spears, C. P. and Danenberg, P. V. Quantitation of thymidylate synthase, dihydrofolate reductase, and DT-diaphorase gene expression in human tumors using the polymerase chain reaction. *Cancer Res.*, 52:108–116, 1992.

Jackmari, A. L., Jones, T. R., Calvert, A. H. *Experimental and Clinical Progress in Cancer Chemotherapy* (F. M. Muggia ED.) Martinus Nijhoff, Boston (1985).

Johnston, P. G., Lenz, H. J., Leichman, C. G., Danenberg, K. D., Allegra, C. J., Danenberg, P. V., Leichman, L. (1995) *Cancer Research* 55:1407–1412.

Leichman, C. G., Lenz, H. J., Leichmian, L., Danenberg, K., Baranda, J., Groshen, S., Boswell, W., Metzger, R., Tan, M., Danenberg, P. V. (1997) *J. Clinical Oncology.* 15(10) :3223–9.

Lenz, H. J., Danenberg, K. D., Leichrnan, C. G., Florentine, B., Johnston, P. G., Groshen, S., Zhou, L., Xiong, Y. P., Danenberg, P. V. and Leichman, L. P. (1998) *Clinical Cancer Research.* 4(5):1227–34.

Sambrook, J. et al., "Molecular Cloning", Cold Spring Harbor Press, 2nd Ed., pp. 9.14–9.23 (1989).

Spears, C. P., Shahinian, A. H., Moran, R. G., Heidelberger, C., and Corbett, T. H. (1982) *Cancer Res.* 42, 450–456; Keyomarsi, K., and Moran, R. G. (1988) *J. Biol. Chem.* 263, 14402–14409.

Swain, S. M., Lippman, M. E., Egan, E. F., Drake, J. C., Steinberg, S. M., and Allegra, C. J. (1989) *J. Clin. Oncol.* 7, 890–899.

What is claimed is:

1. A method for recovering RNA from a biological tissue sample wherein the sample is not an aqueous sample of a bodily fluid, comprising:
   heating the sample in a chaotropic solution comprising an effective concentration of a guanidinium compound to a temperature in the range of about 75 to about 100° C. for a time period of about 5 to about 120 minutes; and
   recovering said RNA from said chaotropic solution using a recovery technique selected from the group consisting of extraction, electrophoresis, chromatography, precipitation, and combinations thereof.

2. The method of claim 1 further comprising rehydrating the sample before heating.

3. The method of claim 2 further comprising homogenizing said sample before beating.

4. The method of claim 3 wherein said RNA is recovered by extraction from said chaotropic solution with a water insoluble organic solvent.

5. The method of claim 4 wherein said water insoluble organic solvent consists essentially of chloroform.

6. The method of claim 5 further comprising purifyng said RNA.

7. The method of claim 6 wherein said RNA is purified by ethanol precipitation.

8. The method of claim 1 wherein said time period is from about 10 to about 60 minutes.

9. The method of claim 8 wherein said time period is from about 30 to about 60 minutes.

10. The method of claim 1 wherein said temperature is in the range of about 85 to about 100° C.

11. The method of claim 10 wherein said time period is from about 30 to about 60 minutes.

12. The method of claim 1 wherein said guanidinium compound is guanidinium hydrochloride.

13. The method of claim 1 wherein said guanidinium compound is guanidinium isothiocyanate.

14. The method of claim 13 wherein said guanidinium isothiocyanate is present in a concentration of about 2 to about 5 M.

15. The method of claim 14 wherein said guanidinium isothiocyanate is present in a concentration of about 4M.

16. The method of claim 13 wherein said chaotropic solution has a pH of about 3–6.

17. The method of claim 16 wherein said chaotropic solution has a pH of about 4.

18. The method of claim 1 wherein said chaotropic solution further comprises a reducing agent.

19. The method of claim 18 wherein said reducing agent is β-mercaptoethanol.

20. The method of claim 18 wherein said reducing agent is dithiothreitol.

21. The method of claim 1 wherein said RNA is used to determine the level of expression of a gene.

22. The method of claim 1, wherein said precipitation is performed with an alcohol.

23. The method of claim 22, wherein the alcohol is ethanol, isopropanol or a mixture thereof.

24. The method of claim 1, wherein said chromatography is ion exchange chromatography, size exclusion chromatography, silica gel chromatography, reversed phase chromatography or a combination thereof.

25. The method of claim 1, wherein said electrophoresis or a combination thereof.

26. A method for recovering RNA from a biological tissue sample wherein the sample is not an aqueous sample of a bodily fluid, comprising:
   heating the sample in a chaotropic solution comprising an effective concentration of a guanidinium compound to a temperature in the range of about 75 to about 100° C. for a time period of about 5 to about 120 minutes; and
   recovering said RNA from said chaotropic solution, wherein the RNA recovered from the chaotropic solution is suitable to determine the level of gene expression by reverse transcription, polymerase chain reaction (RT-PCR) amplification.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: PCR Primer

<400> SEQUENCE: 1
ggcctcggtg tgccttt                                                  17

<210> SEQ ID NO 2
<211> LENGTH: 22
<212> TYPE: DNA
<213> ORGANISM: Artificial Sequence
<220> FEATURE:
<223> OTHER INFORMATION: PCR Primer

<400> SEQUENCE: 2
aacatcgcca gctacgccct gc                                            22

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
gatgtgcgca atcatgtacg t                                             21

<210> SEQ ID NO 4
<211> LENGTH: 18
<212> TYPE: DNA
<213> ORGANISM: Artificial Sequence
<220> FEATURE:
<223> OTHER INFORMATION: PCR Primer

<400> SEQUENCE: 4
tgagcgcggc tacagctt                                                 18

<210> SEQ ID NO 5
<211> LENGTH: 18
<212> TYPE: DNA
<213> ORGANISM: Artificial Sequence
<220> FEATURE:
<223> OTHER INFORMATION: PCR Primer

<400> SEQUENCE: 5
accaccacgg ccgagcgg                                                 18

<210> SEQ ID NO 6
<211> LENGTH: 22
<212> TYPE: DNA
<213> ORGANISM: Artificial Sequence
<220> FEATURE:
<223> OTHER INFORMATION: PCR Primer

<400> SEQUENCE: 6
tccttaatgt cacgcacgat tt                                            22